(12) United States Patent
Gnann

(10) Patent No.: US 8,003,130 B2
(45) Date of Patent: Aug. 23, 2011

(54) METHOD FOR THE PRODUCTION OF MILK OR MILK PRODUCTS WITH A HIGH PROPORTION OF MELATONIN

(76) Inventor: Tony Gnann, Munich (DE)

(*) Notice: Subject to any disclaimer, the term of this patent is extended or adjusted under 35 U.S.C. 154(b) by 802 days.

(21) Appl. No.: 11/921,853

(22) PCT Filed: Nov. 30, 2006

(86) PCT No.: PCT/EP2006/011510
§ 371 (c)(1),
(2), (4) Date: Feb. 13, 2008

(87) PCT Pub. No.: WO2007/068361
PCT Pub. Date: Jun. 21, 2007

(65) Prior Publication Data
US 2009/0324732 A1    Dec. 31, 2009

(30) Foreign Application Priority Data

Dec. 13, 2005 (DE) .......................... 10 2005 059 518

(51) Int. Cl.
*A61K 35/20* (2006.01)
*C07D 209/04* (2006.01)
*A23C 9/00* (2006.01)
*A23L 1/30* (2006.01)

(52) U.S. Cl. ......... 424/535; 548/469; 426/587; 426/648
(58) Field of Classification Search .................. 424/535; 548/469; 426/587, 648
See application file for complete search history.

(56) References Cited

FOREIGN PATENT DOCUMENTS

| GB | 2387099 A | 10/2003 |
|----|-----------|---------|
| WO | 84/00693 A1 | 3/1984 |
| WO | 01/01784 A1 | 1/2001 |

OTHER PUBLICATIONS http://www.milkproduction.com/Library/Scientific-articles/Housing/Light/ Aug. 28, 2002, pp. 1-6, accessed on the Internet on Mar. 22, 2011.
English language Abstract of CN 1537438 A (Database WPI Week 200513, Derwent Publications Ltd., London, GB).
Database FSTA [Online], International Food Information Service (IFIS), Frankfurt-Main, DE; abstract of Stutzer D: "Some questions about night milk." Deutsche Milchwirtschaft, vol. 55, No. 22, pp. 908-909.
Database FSTA [Online], International Food Information Service (IFIS), Frankfurt-Main, DE; abstract of Anonymous: "Swiss regulator turns off the lights on Nachtmilch." New Nutrition Business, vol. 10, No. 6, 2005, pp. 3-4.
Eriksson L. et al., "Diurnal Rhythm of Melatonin in Bovine Milk: Pharmacokinetics of Exogenous Melatonin in Lactating Cows and Goats", Acta vet. scand. 1998, 39, pp. 301-310.

(Continued)

*Primary Examiner* — Rosanne Kosson
(74) *Attorney, Agent, or Firm* — Greenblum & Bernstein, P.L.C.

(57) ABSTRACT

A method for the production of milk with increased melatonin content or a milk product made therefrom. The method comprises dividing the daily cycle of a female mammal into a daytime phase under a first light regime with a proportion of blue light and a night-time phase under a second light regime and milking the mammal at least once during the night-time phase in order to obtain milk with an increased melatonin content. For the second light regime there is used at least one light source which emits light in the wavelength range of 500 nm or above and substantially no light in the wavelength range below 500 nm.

25 Claims, 2 Drawing Sheets

OTHER PUBLICATIONS

Gustafson G. M., "Effect of Changes in Light on Hormonal Secretion and Milk Production of Dairy Cows in Early Lactation", Acta Agric. Scand., Sect. A, Animal Sci. 44: 160-168, 1994.

Sarkar M. et al., "Circardian variations in plasma concentrations of melatonin and prolactin during breeding and non-breeding seasons in yak (*Poephagus grunniens* L.)", Animal Reproduction Science 90 (2005), pp. 149-162.

METHOD FOR THE PRODUCTION OF MILK OR MILK PRODUCTS WITH A HIGH PROPORTION OF MELATONIN

CROSS-REFERENCE TO RELATED APPLICATIONS

The present application is a U.S. National Stage of International Application No. PCT/EP2006/011510, filed Nov. 30, 2006, which claims priority of German Patent Application No. 10 2005 059 518, filed Dec. 13, 2005.

BACKGROUND OF THE INVENTION

1. Field of the Invention

The method relates to a method for the production of milk with a high proportion of melatonin and to milk products that can be obtained from it.

2. Discussion of Background Information

The principal secretion product of the epiphysis or pineal gland is the indolamine melatonin, discovered in 1958 by Lerner and which is produced via serotonin from the amino acid tryptophan. The effects of melatonin were examined in the following years. Positive effects can be achieved through the oral administration of melatonin, so that many possible applications have been developed in human medicine and in the field of nutritional supplements. However, synthetic melatonin of pharmaceutical origin must be used for this, because to date melatonin has not been available in sufficient amounts from natural sources.

Melatonin is a hydrophilic amino acid derivative. In the body it acts as a hormone and anti-oxidant. Numerous neurobiological functions have now been found in humans, such as for example "anti-ageing agent", radical trap, regulator of the circadian clock and endogenous induction of sleep, as well as an influence on reproduction, the immune system, body temperature and brain activity. With humans and also with mammals the hormone melatonin is secreted by the pineal gland. During synthesis the amino acid tryptophan is decarboxylated and hydroxylated. From the serotonin thus formed melatonin is formed by N-acetylation and methylation (=N-acetyl-5-methoxyltryptamin).

The use of milk enriched with melatonin or milk products made from it against the increasing reduction of the melatonin level with age would be a logical concept, for example, from a scientific point of view. The daily level of melatonin in the blood is about 20 to 70 pg/ml for young people (20-30 years old). It increases at night to about 125 pg/ml. This range of concentration would have to be reached after the consumption of milk or milk powder. With oral administration melatonin is however subject to a relative high first-pass mechanism, i.e. about 30% is metabolised by the liver and eliminated and therefore does not occur at an effective level in the blood. Therefore, about a 30% higher amount has to be taken orally to obtain the desired target concentration.

Melatonin from natural sources is to date only available with restrictions. Previously slightest concentrations have been found in a few species of plants. There is however no method for the systematic extraction and no natural store for keeping foodstuff rich in melatonin. Studies and research into the medicinal effectiveness and biological availability of naturally produced melatonin have to date not been published. The extent to which naturally extracted melatonin differs from the pharmaceutically produced melatonin with regard to its biological effect and availability has to date not been sufficiently investigated.

It is known that melatonin occurs in traces in the blood plasma of humans and mammals and is continuously reproduced. Melatonin bound to blood plasma is however not suitable for use in human medicine or as a nutriment or nutritional supplement.

In contrast, a well-known foodstuff produced with the aid of blood in the body of various mammals is suitable for the extraction of natural melatonin, namely milk. Here, the melatonin is in particular bound to the milk protein.

For humans it is known that the change of light irradiation is important for the control of the behaviour related to the time of day and seasons. The light/darkness cycles control many behavioural patterns of humans, including winter depression, sleeping/awake cycles, body temperature, brain activity, subjective awareness and performance. These influences known in humans also largely apply to mammals.

All animals are adapted to the cyclic change of day and night. So-called internal clocks control all important life functions such as the metabolism, body temperature, the hormone and immune systems as well as the behaviour on a daily cycle. The 24-hour cycle of this internal pacemaker is however not controlled by external time information. This so-called circadian system also functions in the absence of external factors, but does not correspond exactly to one day. The expression "circadian" is derived from the Latin expressions "circa" (approximately) and "dies" (day).

The synchronisation of the internal pacemaker with the external day/night cycle occurs via time generators, external stimuli, which convey information about the time of day to the body. The most important time generator for mammals is light. But also factors such as temperature, activity and social interaction can offset the circadian cycle. There are many indicators that the circadian system with mammals can be synchronised by light exclusively via the retina, wherein information about the light conditions is essentially received through retinal photoreceptors.

The normal husbandry methods now employed for lactating mammals allow the animals to move freely and they can freely go to their bedding down, feeding and milking positions both during the daytime and at night. The livestock quarters are usually equipped with white-coloured emergency lights at night, so that the animals can differentiate between friend and foe and can find their desired destinations. Conventional illumination systems of this nature reduce the production of melatonin in the night.

In WO 01/01784 a method for the production of milk rich in melatonin is described in which the daily cycle of mammals is divided into one light and one dark period and the animals are milked at the end of the dark phase. The amount of light during the dark period is preferably below 40 lux. Also in GB-A-2387099 a method for the production of milk rich in melatonin is described in which the daily cycle of mammals is divided into one light and one dark period, wherein the light intensity in the dark period should not exceed 50 lux. Also experiments in darkening and the use of black light in the dark period are described.

The previously known methods have a common feature in that in the "dark phase" of keeping the animals the lowest possible amount of light is regarded as mandatory. This is however associated with difficulties, because the animals can only orientate themselves with difficulty or not at all during this dark phase due to the lack of or inadequate light, which is not practicable in particular during the milking process. The melatonin content of the milk is thus negatively influenced.

In particular if the animals are kept in a shed and in a large number, the lack of orientation represents a serious problem. Therefore the above described methods are at best suitable for small farms. For larger herds of animals in free-ranging systems these methods are hardly practicable according to the state of the art. Industrial production relevant to the market is thus hardly possible.

The object of the invention under consideration is therefore the provision of a method for the production of milk with increased melatonin content which facilitates adequate orientation for the animals and also for the operating personnel during the night and which is also suitable for an increased number of animals.

These objects were surprisingly able to be solved by a method for the production of milk with increased melatonin content or milk products of it, in which the daily cycle of one or more female mammals is divided into a daytime phase under a first light regime with a proportion of blue light and a night-time phase under a second light regime and the animal or animals are milked at least once during the night-time phase in order to obtain milk with a high melatonin content, characterised in that during the night-time phase at least one light source is used for the light regime, which emits light in the wavelength range of 500 nm or more and essentially no light is emitted in the wavelength range below 500 nm. The light source in particular emits light of the colour yellow, orange, amber or red or a mixed colour of these, wherein red light is especially preferred.

With the invention presented here a method is described in which, with the use of appropriate light regimes, the circadian cycle and the melatonin suppression in the animals are influenced such that milk with increased melatonin content is obtained. In achieving this, the animals are despite this kept in the night-time phase under a light regime which ensures adequate orientation. Thus, the method can also be employed with a larger number of animals.

SUMMARY OF THE INVENTION

The present invention provides a method for the production of milk with increased melatonin content or a milk product made therefrom. The method comprises dividing the daily cycle of at least one female mammal into a daytime phase under a first light regime with a proportion of blue light and a night-time phase under a second light regime and milking the mammal at least once during the night-time phase in order to obtain milk with an increased melatonin content. For the second light regime during the night-time phase there is used at least one light source which emits light in the wavelength range of 500 nm or above and substantially no light in the wavelength range below 500 nm.

In one aspect of the method, the at least one light source may exhibit at least one maximum above 550 nm in the wavelength range of visible light.

In another aspect of the method, the at least one light source may comprise a luminescent radiator and/or the at least one light source may comprise an LED lamp and/or a sodium vapor lamp. For example, the LED lamp may emit red, yellow, orange or amber-coloured light or a mixed color thereof. Preferably, the LED lamp emits red light.

In yet another aspect to the present method, the at least one female mammal may be a sheep, a goat and/or a cow. In another aspect, the at least one female mammal may comprise a group of lactating animals.

In a still further aspect of the method of the present invention, the at least one female mammal may be milked at least twice during a 24-hour period and the milk obtained during the daytime phase may not be used for providing the milk with increased melatonin content.

In another aspect of the method, the at least one light source may be used in the night-time phase at least during the milking process and/or for at least two hours, preferably during substantially the entire night-time phase.

In yet another aspect of the method, one or more full-spectrum lamps, sunlight and/or one or more other light sources with a high circadian effect may be used for the first light regime in the daytime phase.

In another aspect of the method, the daytime phase may last longer than 14 h.

In a still further aspect, the method may further comprise an extraction of lactose from the milk and/or a fat reduction of the milk.

In another aspect, the at least one light source may produce a luminous intensity of more than 50 lux, for example, more than 100 lux.

In yet another aspect, the method may further comprise the conversion of the milk which is enriched with melatonin to milk powder.

In another aspect, the method may increase the milk capacity of the at least one female mammal.

The present invention also provides a milk powder which is obtainable by the method of the present invention as set forth above (including the various aspects thereof) and has a melatonin concentration of more than 150 pg/g.

The present invention also provides a nutriment, nutritional supplement or medicament which comprises the milk, milk product or the milk powder which is obtainable by the method of the present invention as set forth above (including the various aspects thereof).

DETAILED DESCRIPTION OF THE INVENTION

Figure 1:
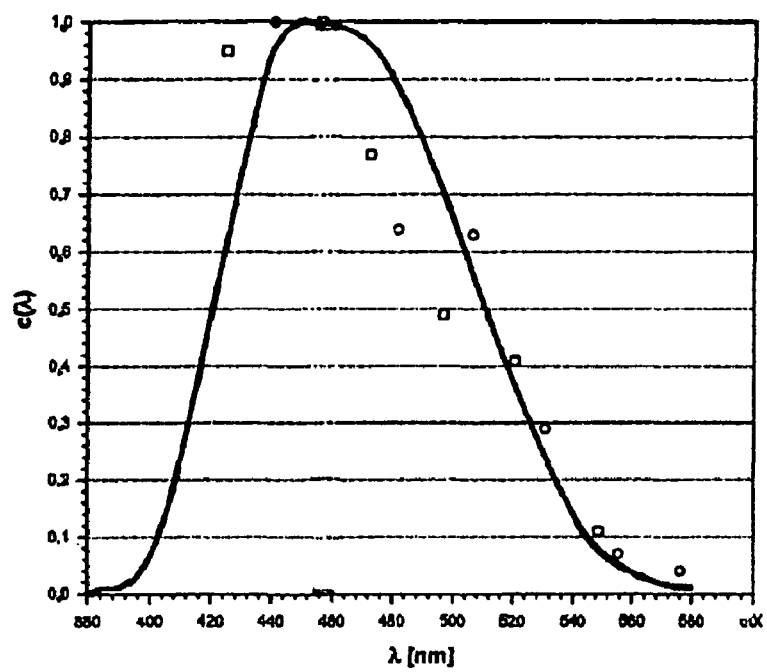
FIG. 1 shows an averaged circadian response curve in dependence on the wavelength of the light.

For the production of milk protein highly enriched with melatonin all lactating animals are suitable, in particular female animals selected from the mammalian breeds sheep, cows and goats. Due to their physiological prerequisites, these three animal species offer an ideal economical ratio of body weight to milk yield. They have similar circadian cycles and systems and natural milk stores (udders). In addition they are widespread in populations throughout the world with good availability.

One or more animals are kept under the daily cycle according to the invention, preferably at least 10, more preferably at least 50 or 100 or even more than 200 animals. Preferably a group of lactating animals are subjected to the cycle according to the invention. Keeping the complete group under the daily cycle according to the invention is advantageous, because then no special intervention is required, the animals experience no unusual changes and different animal husbandry required due to separation can be avoided.

Unless otherwise stated, here light is taken to mean the visual radiation incident on the eye, which causes a sensation of vision, i.e. radiation in the wavelength range from 380 to 780 nm. The luminous intensity is generally defined as the amount of light incident on an area and not the quantity of light which impinges on the retina. The latter is however decisive for the circadian effect of the light. It is not the light intensity of a light source in lux, but the colour of the light and the wavelength of the light colours which are important for the desired effect on the circadian system which is important for the melatonin production.

As light sources only those are accordingly considered which emit light in the visible range. The spectral distribution of the light produced by light sources becomes clear in emission spectra in which the intensity is given in dependence on the wavelength. Often the relative intensity is given, wherein the highest value in the examined spectrum is set to 100%.

The amount of light, its spectral composition, spatial distribution and the time and duration which are required for mammalian vision differ significantly from requirements arising from circadian functions.

Among other things, the invention is based on the dependence of melatonin suppression on the spectral composition of the light source employed. Through the invention the optimally adapted lighting with artificial light can be achieved for a maximum yield of melatonin. For this, the colour parameters of various light sources were investigated in relationship to their effectiveness for melatonin suppression.

Light is the primary stimulant for the control of melatonin formation. The use of selected light sources for a specific effect on circadian functions produces a controlled suppression or stimulation of the melatonin secretion by the pineal gland due to different light regimes and consequently results in an increased melatonin concentration in the blood plasma. The melatonin content in the blood plasma correlates, somewhat differently and offset in time, with the melatonin concentration in the milk.

A new type and combination of light sources and colours are used, because the quantity of the light source, the spectrum of the light colours and their wavelength, the spatial distribution and the time and duration of the applied light for the circadian influence of the animals are completely different to those which are important for normal vision. It has been found that for influencing the melatonin level in the blood of mammals there is light which is well suited and there is light which is unsuitable. The light systems which have been found are suitable for precisely controlling photopic and also circadian effects of light for melatonin suppression.

The adaptation of the physiological and psychological processes of the body to the temporal ambient conditions occurs through the internal clock. With the elimination of time generators the internal clock runs freely. Thus for example, in complete darkness the free running circadian period of the human being lasts on average 10 min to 20 min longer than the 24-hour day. Disturbances in the synchronisation of the internal clock and the erroneous daily cycle resulting from it are highly effective in the negative sense with regard to melatonin production. The adaptation of the circadian daily period to the current day/night cycle occurs through the light absorbed by the retina and the mechanism of melatonin suppression.

It is not the luminous intensity of a light source measured in lux that is decisive for the melatonin suppression, but rather the spectral dependence. It has been found that in comparison to the brightness sensitivity curve for daytime vision, the spectral sensitivity of the circadian photoreceptors can be influenced, primarily by the short-wave region of the visible spectrum. This results, for example, in the blue portions of the light being more effective in the control of the circadian system than other spectral colours.

Consequently, from the viewpoint of the best possible efficiency of the melatonin production, the spectral sensitivity, i.e. the dependence of the efficiency on the wavelength, is of great importance. Here, a differentiation must be made between the photopic or scotopic effect of the light and the circadian effect of the light—that is the effect on the melatonin production.

Figure 2:
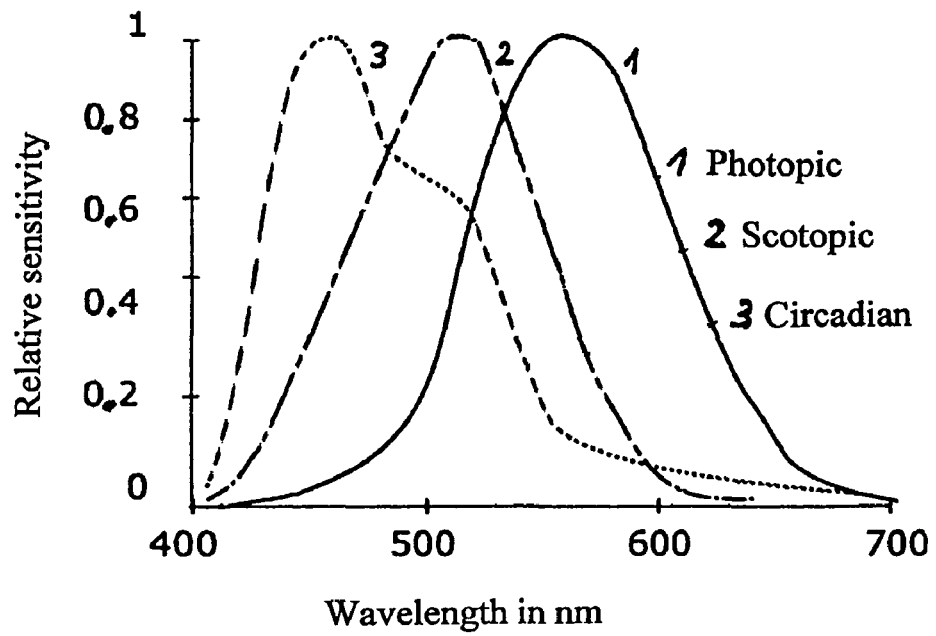
FIG. 2 compares the wavelength dependence of the photopic, scotopic and circadian effects. Photopic relates to vision with normal brightness. Scotopic relates to vision in the twilight or in darkness.

FIG. 1 shows a circadian response curve in dependence on the wavelength of the light. FIG. 2 shows sensitivity curves for the photopic, scotopic and circadian effect in dependence on the wavelength.

Photopic and circadian luminous efficiencies differ substantially depending on the type of the selected light source. Dimensioning of the luminous efficiency in lux or lumens per watt is therefore not suitable for the assessment of the melatonin suppression. The maximum effectiveness of the melatonin suppression occurs with light in the wavelengths from approx. 450 to 470 nm. These wavelengths are contained in the spectral colour range of sunlight and in the artificial light colour "blue". The photopic and circadian effects of various light sources are given by examples in the following table.

| Light source | Luminous efficiency (photopic) (lm/W) | Luminous efficiency (circadian) (lm/W) | Ratio of the luminous efficiency, circadian/photopic |
|---|---|---|---|
| 3000 K fluorescent rare earth | 87 (1.00) | 149 (1.00) | 1.00 |
| 4100 K fluorescent rare earth | 87 (1.00) | 275 (1.85) | 1.85 |
| 7500 K fluorescent rare earth | 65 (0.75) | 285 (1.91) | 2.56 |
| Sulphur-scandium metal vapour | 108 (1.24) | 300 (2.02) | 1.63 |
| Sulphur high pressure | 127 (1.46) | 115 (0.07) | 0.53 |
| LED red (630 nm) | 44 (0.51) | 2 (0.02) | 0.03 |
| LED yellow (590 nm) | 36 (0.41) | 10 (0.07) | 0.17 |
| LED green (520 nm) | 25 (0.29) | 88 (0.59) | 2.06 |
| LED blue (460 nm) | 11 (0.13) | 681 (4.59) | 36.2 |
| LED white (460 nm + fluorescent) | 18 (0.21) | 90 (0.60) | 2.91 |
| Daylight (6500 K) | — | — | 2.78 |

The photopic luminous efficiency, referred to a fluorescent lamp with 3000 K (Kelvin), is 44 for an LED in the spectral colour red, but 11 with the LED in the colour blue. The circadian luminous efficiency, referred to a fluorescent lamp with 3000 K, is 2 for an LED in the colour red, but 681 with the LED in the colour blue.

For the melatonin content it is only relevant that coloured light sources with the maximum luminous efficiency in the short-wave range maximise the circadian effect and coloured light sources in the long-wave range minimise it. For example, a blue LED (maximum approx. 460 nm) and a red LED (maximum approx. 630 nm) have about the same photopic luminous intensity. The circadian luminous efficiency of these two colours differs however approximately in the ratio 1200:1.

The ratio of the relative circadian to photopic luminous efficiencies referred to a fluorescent lamp with 3000 K with an LED in the colour red reaches the best possible efficiency for the promotion of melatonin formation. A reduced, but adequate effect is obtained with an LED in the colours amber, orange or yellow or with mixed colours of these spectra or through the use of a sodium vapour lamp with the colour yellow.

The daylight phase is a phase of maximum melatonin suppression controlled by specific application of light, preferably during the day by using the natural daytime brightness, whereas the night-time phase is a phase of maximum inhibition of the melatonin suppression controlled by specific application of light, preferably at night using natural darkness.

Accordingly, the daily cycle of the animals is divided into a daytime phase under one light regime and a night-time phase under a different light regime. In particular the light regime of the daytime phase involves a light regime with a proportion of blue light. In the night-time phase the light used essentially exhibits no proportion of blue light.

The light regimes according to the invention can be controlled principally as required with regard to intensity and temporal application. The respective phases can be shortened, lengthened or displaced forwards or backwards as necessary. However, circadian cycles can only be changed very slowly, because the circadian system is very inert. Therefore, it may be practicable to change the daily cycle slowly, e.g. in a number of stages, to the required daily cycle and/or to start with the actual extraction of milk with the increased melatonin content only after a familiarisation phase, e.g. of a few days.

Irrespective of the fact that the application of light can be controlled temporally as required, it is advantageous if the daytime phase lasts, for example, about 8 to 22 hours, practicably about 12 to 21 hours and preferably about 14 to 20 hours. A favourable duration is, for example, about 17 hours plus/minus 1 hour or more. The night-time phase can, for example, last about 2 to 16 hours, practicably about 3 to 12 hours and preferably about 4 to 10 hours. A particularly favourable duration is, for example, about 6 hours plus/minus 1 hour or less.

The daytime phase is here the phase of suppression of the melatonin formation, whereas in the night-time phase the suppression is inhibited. In order to exploit the daily bright and dark phases, the daytime and night-time phases should be oriented towards them. This is however not principally necessary, but is efficient in terms of practical considerations. The daytime phase (suppression phase) could, for example, be arranged in the time from approx. 5.00 hrs. to 22.00 hrs. and the night-time phase (inhibition of the suppression phase) in the time from approx. 22.00 hrs. to approx. 5.00 hrs. Of course, the phases can also be arranged with other time intervals.

The transition from one phase into the other phase should in each case preferably simulate a brightness and darkness transition, which is modelled on the natural light transition from night to day and vice versa. Any disturbance of the usual cycles impairs the melatonin secretion. A transition of this nature can, for example, last approx. 30 min to 1.5 hours, preferably approx. 1 h. The transition time can be added half each to the daytime and night-time phases.

The daytime phase and the night-time phase are each characterised by a different light regime. Both light regimes can be controlled by artificial light; in the daytime phase the use of normal sunlight is practicable.

In the daytime phase the animals are in particular subjected to a light regime with a proportion of blue light which exhibits a high photopic and circadian effect. Blue light is light which lies in the wavelength range from approx. 440 to 490 nm. A maximum melatonin suppression can be achieved by the animals going out into the sunlight or through the application of light sources with a high circadian effect. According to the invention full-spectrum lamps (approx. 375-725 nm) are preferred, which are most similar to sunlight (approx. 290-770 nm) and include important UV light as well as the known colour spectrum of the rainbow. Irradiation simulating sunlight over several hours also causes the maximum melatonin suppression through a strong effect on the circadian system.

Full-spectrum lamps are commercially available. Examples are the luminous colour 940 white from Osram or Biolux from Osram with the luminous colour 965. The latter is preferred, because it approximately simulates the sun's spectrum. Similar full-spectrum lamps are also offered by other manufacturers.

Apart from sunlight and full-spectrum lamps, other light sources can also be employed which suppress the production of melatonin through high circadian action. The use of blue light (wavelength approx. 460 nm) would be possible for example or other light sources with a proportion of blue light with which a high melatonin suppression is achieved. With the use of blue light the risk of the thermal retinal hazard, which is dependent on the wavelength, should be taken into account.

With a light regime through artificial light such as full-spectrum lamps, the daytime phase can also be lengthened or shortened as required. The milk capacity of the lactating animals is significantly increased by extending the brightness phase.

In the night-time phase the animals are subjected to a light regime which inhibits the melatonin suppression and therefore promotes melatonin formation. The maximum inhibition of the melatonin suppression would be in principle achieved by natural darkness (lack of light). However, this produces the disadvantage in that orientation is no longer possible. Above all, this is not practicable during the milking process. In addition the loss of orientation causes stress for the animals, primarily when they are kept in large numbers and in restricted surroundings. This also impairs the formation of melatonin.

Black-light lamps are UV lamps (approx. 345-400 nm) which influence the circadian system only slightly, but due to their low photopic luminous efficiency are not suitable for the night-time phase, in particular in free-range systems, because no adequate orientation can be achieved due to the low luminous intensity. As well as UV light, black-light lamps can also emit visible light in the blue range.

It has been surprisingly found that these disadvantages can be overcome if, to counteract the darkness, light sources are used which emit light in the wavelength range of 500 nm or more and in the wavelength range below 500 nm essentially do not emit any light, so that the light source in particular emits light of the colour yellow, orange, amber or red or a mixture of these colours. Therefore, in the wavelength range of visible light the light source exhibits an emission spectrum which has the highest value with a relative intensity of 100% at a wavelength of 500 nm or more.

That the light source essentially emits no light with a wavelength below 500 nm signifies in particular that in the emission spectrum of the visible light below 500 nm any measurable value, if present at all, exhibits a relative intensity of less than 15%, preferably less than 10% and especially preferably less than 5 or less than 3%. Preferably the applied light source emits essentially no light in the wavelength range below 520 nm and preferably below 540 nm. Especially preferably, the applied light source emits no light in the wavelength range below 500 nm and in particular below 520 nm and more preferably below 530 nm.

As light sources normal lamps such as for example thermal radiators, continuum radiators, line radiators and gas discharge lamps can be used which contain a monochromator, so that essentially no light with a wavelength below 500 nm is emitted. Examples of monochromators are prisms, diffraction gratings and optical filters. As filters, for example, interference filters, band pass filters or long pass filters which block the short-wave regions are suitable. Filters of this nature are, for example, available from Schott. Red-light lamps can be manufactured in this way. Red-light lamps with adequate blocking of blue-light content can be used in the invention under consideration.

Light sources of this nature, which operate with filters or other monochromators, also have some disadvantages. One aspect is that wavelength ranges are not completely cut off, but rather increasingly reduced. Also, faults in the barrier lead to small peaks at other wavelengths or harmonics in the pass region, so that slight amounts of light can also be present in the range below 500 nm. Thus red-light lamps are not purely red in colour, but rather they can also contain slight proportions of other spectral colours. Additionally, part of the light produced is not used for lighting, but is instead filtered out. This increases the energy consumption.

Therefore, light sources are preferred which do not require any monochromator. Accordingly, preferably no thermal radiators are used. Preferably luminescent radiators are used as the light source. Luminescent radiators can be so-called line radiators or monochromatic radiators. Examples of luminescent radiators are gas discharge lamps and light emitting diodes. Therefore for a light source a luminescent radiator is preferably used which essentially emits no light with a wavelength below 500 nm or no light at all with a wavelength below 500 nm.

The emission spectrum of the light source in the wavelength range of visible light has preferably at least a maximum above 550 nm, preferably at least a maximum above 570 nm and more preferably above 600 nm. The light source preferably has no maximum below 550 nm, more preferably below 570 nm and still more preferably below 600 nm in the visible wavelength range with a relative intensity of more than 5%.

It has been found that it is important in the night-time phase to use light in which light with wavelengths of less than 500 nm, better less than 520 nm and still better less than 550 nm is minimised and preferably essentially completely or completely avoided. This is possible with light sources which exhibit a continuous spectrum if suitable filtering is applied. Luminescent radiators, such as LEDs and SVLs, are however preferred, because, in contrast to thermal radiators, they radiate a narrow-band spectrum and require no filtering. Through the method according to the invention improved orientation of the animals can be achieved due to the far higher photopic effect of the light sources used, in particular of the luminescent radiators.

A suitable light source is, for example, a sodium vapour lamp (SVL). SVLs are gas discharge lamps, which are characterised by high photopic luminous efficiencies and emit monochromatic yellow light with a wavelength of approx. 589 to 590 nm. Lighting with SVLs is suitable for reliable recognition of objects and obstructions. The yellow light should also be less attractive to insects.

Figure 3:
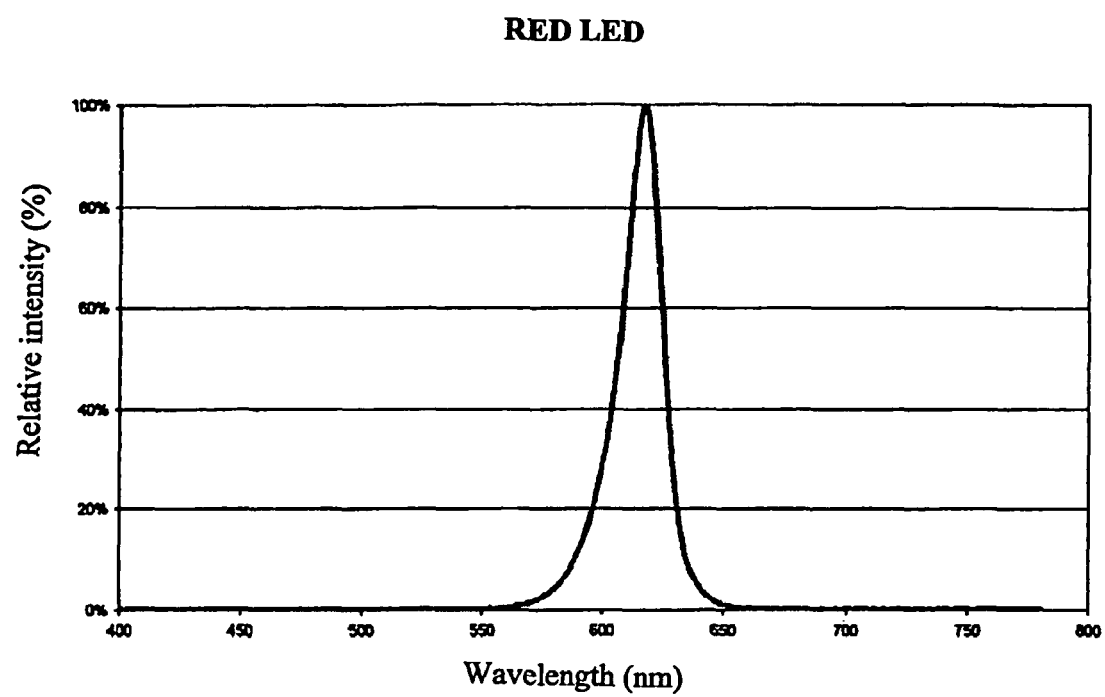
FIG. 3 shows the spectral distribution of a red LED.

Particularly suitable luminescent radiators are light-emitting diodes, also known as LEDs. LEDs are very efficient light sources. They usually exhibit a relatively narrow-band signal with a maximum in the emission spectrum as illustrated, for example, in FIG. 3. With LED lamps the desired wavelength range can be specifically set and they also have an adequately large photopic effect, so that the animals can easily orientate themselves under lighting with these light sources.

As a light source for the night-time phase light sources are selected which have a low circadian luminous efficiency. The primary factor is the choice of the correct luminous colours. Blue LEDs or white-light LEDs are not suitable due to the proportion of blue light. Ideal luminous colours are red, less good, but also possible are amber (also "superorange") (e.g. maximum approx. 612 nm), orange (e.g. maximum approx. 605 nm) or yellow (e.g. maximum approx. 585 nm) as well as mixed colours of these spectra. Yellow light can also be produced by an SVL. Red light-emitting diodes are preferred (e.g. maximum approx. 630 nm; including "ultrared" with a maximum of approx. 660 nm) which have a photopic luminous efficiency that is very high despite minimal circadian effect and which are therefore ideally suitable for night-time operation. Additionally, LEDs are the sole illuminants which supply red light in a pure colour. LEDs of this nature are widely commercially available.

Examples of LEDs obtainable commercially and which are practicable for the invention are, for example, Lumileds® Luxeon red 1 watt, Lumileds® Luxeon Star/O red 1 watt or SOUL R32 red 1 watt.

It is not necessary to use the light source during the complete night-time phase. It is, however, in particular at least used during the milking process, because then the necessity for orientation amongst the animals and operating personnel is the greatest. Preferably the light source is in use during at least one third or at least half of the duration of the night-time phase. Because the light source used, primarily the luminescent lamp, has practically no negative effect on the melatonin formation and with it an improved orientation for the animals and operating personnel is also possible, the light sources are particularly preferably used essentially during the complete night-time phase or throughout the night-time phase. The light source, in particular the LED lamp, is used during the night-time phase normally at least 1 hour, preferably at least 2 hours, more preferably at least 5 hours and still more preferably at least 6 hours.

Otherwise, no other light sources should be used in the night-time phase. However, no total darkness is necessary. In combination with the light source or sources for the night-time phase, the natural darkness of the night is quite practicable. In particular essentially no illumination with light with a blue-light content (in particular from 450 to 470 nm) is present.

It should be noted that a natural system is involved so that short-term disturbances of the system (thunderstorms, lack of light, etc.) and variations (adaptation to the season by displacement of the daytime and night-time phases) are possible and comprised by the method of the invention.

In order that the light regimes of the daytime and night-time phases are fulfilled, the light sources should preferably be installed both in height and frequency such that the light effect can develop in all areas accessible to the animals. With the use of sunlight the areas accessible to the animals should of course be appropriately selected.

Determination of the luminous efficiency in lux for the purpose of inhibiting or stimulating the melatonin suppression is practically irrelevant with regard to the melatonin production, because properties of the applied light have to be considered both according to the relevant aspects for the circadian system as well as for the visual system. It is not the intensity of a light source in lux, but the colour of the light and the wavelength of the luminous colours which are decisive for the desired effect on the circadian system which is important for melatonin production.

Surprisingly the surroundings of the animals can even be relatively brightly illuminated in the night-time phase with the light sources used according to the invention without this leading to a significant reduction in the melatonin concentration in the milk. This stands in contrast to the previous state of the art in which the darkest ambient conditions possible are assumed to be necessary. This has the decisive advantage in that orientation is substantially easier and the lighting can be switched on without further ado during the complete night-time phase.

The luminous intensity, obtained through the light sources used in the night-time phase, can preferably be more than 50 lux, more preferably more than 100 lux and particularly preferably more than 250 lux. The luminous intensity can for example be 500 lux and more. The luminous intensity can be measured with normal light meters. For line sources, such as LEDs, spectro-radiometers can be used for more precise measurements. The luminous intensity is referred to the radiation incident on the eye of the animal. Thus, the specified luminous intensity is measured at the eye height of the animals. In this way the specified luminous intensity for cows is measured at a level of about 1.50 m from the ground and with goats at a level of about 50 cm from the ground.

With the luminous intensity it must however be taken into account that long-wave light, such as defined here, also exhibits a circadian effect, even if it is extremely low, which increases in the direction of shorter wavelengths. With high luminous intensities this circadian effect can influence the melatonin content. Therefore, with luminous intensities of more than 50 lux in particular it is preferable to use a light source which emits light with a wavelength maximum above 620 nm, such as a red LED.

The relevant animals are milked at least once in the night-time phase. Depending on the number of animals to be milked, the start of the milking process is arranged such that it is concluded before the end of the night-time phase. The milking process starts, for example, practically in approximately the middle of the night-time phase, in particular when a larger number of animals are to be milked, in order to be able to milk all animals in the night-time phase. The milk obtained in this way has an increased melatonin content. The hormone melatonin is converted in the liver principally to 6-sulphatoxymelatonin and eliminated via the kidneys. The half-life is less than about 60 minutes. For the retention of the melatonin level in the milk, the inhibition of the melatonin suppression must be maintained up to the end of the milking process of the animal, i.e. the milking process takes place in the night-time phase with illumination by the light source.

The stronger and longer the suppression is, the higher is the melatonin peak then obtained in the milk. Therefore, through shortened night-time phases under a light regime with the lowest possible circadian effect and milking at the end of the night-time phase, milk with a higher melatonin concentration can be obtained. For example, extended daytime phases of 16 h and preferably more than 18 h are suitable for obtaining an increased melatonin peak in the night-time phase. The light exposure for the daytime phase can then follow immediately after the milking process.

The animals can of course be milked more than once each day and as required, e.g. twice or more frequently. Preferably milking also occurs at least once during the daytime phase. Since this milk does not exhibit any increased melatonin content, it is also used separately from the milk with increased melatonin content collected in the night-time phase.

The milk collected during the night-time phase is preferably quickly cooled to below 10° C., for example 3 or 8° C. Here, quickly means, for example, within two hours or less. The milk can be processed in the normal way to give all the familiar milk products, wherein milk products with an increased melatonin content are obtained. The milk products obtained from milk, such as milk powder, and the methods for the manufacture are well known. A general description can be found, for example, in Ullmanns Encyklopädie der technischen Chemie [Ullmann's Encyclopedia of Industrial Chemistry], 4th edition, volume 16, p. 689 ff. Examples of milk products are milk powder, cheese, yoghurt, quark and whey products. Preferably the milk is converted to milk powder with a high melatonin content by drying. The generally known methods can be used for this. The hormone melatonin is bound to the protein molecules in the milk and is not destroyed by pressure, heat or freezing treatment.

The milk or the milk products, in particular milk powder, can be used for normal applications, in particular as or for nutriments, nutritional supplements and medicaments. Through further treatment of the milk in the form of fat reduction or lactose extraction, the relative proportion of melatonin in the final product (e.g. milk, powder from full-cream milk or skimmed-milk) can be increased further.

Normal daily milk contains melatonin values of approx. 1.5-3 pg/ml. The milk produced following the method according to the invention generally contains at least twice that amount or even up to ten times the amount or more. It can, for example, exhibit a melatonin content of more than 10 pg/ml, e.g. 15-50 pg/ml. Milk enriched with melatonin, which is obtained according to the method of the invention, can be processed such that the concentration of the hormone melatonin bound to the molecules of the milk protein in the final product is significantly increased by up to 350 times the melatonin concentration normally present in milk.

The milk powder that can be obtained has, for example, a melatonin concentration of over 100 pg/g, preferably over 150 pg/g and more preferably more than 200 pg/g. The melatonin concentration can, for example, amount to 1,000 pg/g as required. A marketable final product in the form of milk power, obtained according to the invention, contains, for example, a melatonin concentration of about 200 to 500 pg/g. With a concentration increased in this way numerous possible uses in the medicinal field and as nutriments or nutritional supplements are possible. The milk powder can, for example, be provided with or without compatible carriers, for example, as powder, capsules, solution or tablets. It can be mixed with other suitable additives and/or active ingredients, such as nutrients, for example, vitamins or minerals or pharmaceutical active ingredients.

The method according to the invention is suitable for sustainable, industrial production of natural melatonin, particularly also for production in operations with over 200 animals. The natural melatonin is here bound to milk protein. Thus, natural melatonin, bound to milk protein, can be produced in large quantities and in a simple manner, preferably in the form of milk powder.

Through the method according to the invention, the objectives that can be achieved include the following:

1. The natural circadian cycle of the animals is supported and daily temporal information is signalled to the body.
2. Through the installation and control of the light sources used according to the invention in the rooms where the animals are kept, the production of the hormone melatonin in the blood serum and thus also in the milk is stimulated such that the concentration of melatonin in the milk increases to many times the normal concentration. In the average herd melatonin values in the final product of over 200 pg/g of milk powder are obtained with individual animals reaching values of over 500 pg/g.
3. Through the temporally specific application of the above mentioned light sources, the daily brightness and darkness phases are specifically manipulated such that the melatonin secretion of the pineal gland is maximally suppressed or maximally stimulated, so that within a precisely determinable period of the day the highest possible melatonin concentration in the milk is obtained and through precisely timed milking of the animals milk with a melatonin concentration increased many times is obtained.
4. In the rooms where the animals are kept it is possible to dispense with the previously normal emergency lighting using white light (e.g. filament, neon or fluorescent lamps).
5. Darkening of the rooms accommodating the animals to avoid incident light is not required, because the natural darkness of the night and the use of the above mentioned light sources are adequate in inhibiting the melatonin suppression.

EXAMPLES

The influence on dairy cows from various light sources has been examined with regard to the achievable melatonin content. The investigation took place on a large herd, wherein the light regime of the daytime and night-time phases was varied in Examples 1 to 3. During the night-time phase randomly selected dairy cows were milked and the melatonin content in the milk determined.

The selected light regime and the average melatonin contents found in the milk are summarised in the following table.

|  | Example 1 | Example 2 | Example 3 (Comparison) |
|---|---|---|---|
| Light regime, daytime phase | Artificial daytime lighting with white light, 16 h | Natural light | Natural light |
| Light regime, night-time phase | Only light from red light-emitting diodes** | Only light from red light-emitting diodes** | White emergency light |
| Melatonin* | 20.35 | 10.25 | 4.57 |

*Average melatonin content of the milk (pg/ml);
**Wavelength 600 to 640 nm

It can be immediately seen that a clearly increased melatonin content can be achieved through the method according to the invention. Details about the milking plan in the examples are given in the following tables.

Example 1

| Sample no. | Animal no. | Morning milking time | Melatonin in pg/ml |
|---|---|---|---|
| 1 | 205 | 05:00 | 9.95 |
| 2 | 392 | 05:00 | 33.40 |
| 3 | 305 | 05:10 | 10.72 |
| 4 | 312 | 05:10 | 31.11 |
| 5 | 303 | 05:10 | 10.71 |
| 6 | 252 | 05:10 | 13.69 |
| 7 | 375 | 05:20 | 32.98 |
| 8 | 277 | 05:25 | 32.49 |
| 9 | 298 | 05:25 | 27.49 |
| 10 | 233 | 05:30 | 17.79 |
| 11 | 299 | 05:35 | 32.03 |
| 12 | 386 | 05:40 | 11.15 |
| 13 | 241 | 05:45 | 14.53 |
| 14 | 286 | 05:50 | 11.68 |
| 15 | 250 | 05:50 | 24.18 |
| 16 | 322 | 05:50 | 26.77 |
| 17 | 234 | 05:50 | 16.44 |
| 18 | 319 | 05:50 | 33.48 |
| 19 | 257 | 04:50 | 13.16 |
| 20 | 237 | 04:50 | 22.26 |
| 21 | 255 | 04:40 | 24.12 |
| 22 | 331 | 04:50 | 10.97 |
| 23 | 315 | 04:50 | 14.40 |
| 24 | 356 | 04:50 | 11.79 |
| 25 | 403 | 04:55 | 32.08 |
| 26 | 280 | 04:55 | 10.62 |
| 27 | 254 | 04:55 | 11.35 |
| 28 | 212 | 05:50 | 9.73 |
| 29 | 276 | 05:30 | 32.14 |
| 30 | 344 | 06:10 | 11.80 |
| 31 | 309 | 06:10 | 34.11 |
| 32 | 316 | 05:10 | 22.14 |
|  |  | Average | 20.35 |

Example 2

| Sample no. | Animal no. | Morning milking time | Melatonin in pg/ml |
|---|---|---|---|
| 1 | 17 | 05:00 | 3.30 |
| 2 | 205 | 05:00 | 17.79 |
| 3 | 314 | 05:10 | 5.53 |
| 4 | 303 | 05:10 | 11.79 |
| 5 | 256 | 05:10 | 4.15 |
| 6 | 34 | 05:10 | 9.47 |
| 7 | 386 | 05:20 | 16.44 |
| 8 | 254 | 05:25 | 14.53 |
| 9 | 286 | 05:25 | 11.68 |
| 10 | 356 | 05:30 | 10.71 |
| 11 | 257 | 05:35 | 13.16 |
| 12 | 366 | 05:40 | 7.35 |
| 13 | 315 | 05:45 | 9.95 |
| 14 | 370 | 05:50 | 8.56 |
| 15 | 241 | 05:50 | 11.15 |
| 16 | 234 | 05:50 | 11.35 |
| 17 | 233 | 05:50 | 10.62 |
| 18 | 237 | 05:50 | 22.26 |
| 19 | 330 | 04:50 | 9.28 |
| 20 | 250 | 04:50 | 10.72 |
| 21 | 322 | 04:40 | 10.97 |
| 22 | 270 | 04:50 | 6.44 |
| 23 | 312 | 04:50 | 9.73 |
| 24 | 227 | 04:50 | 9.27 |
| 25 | 403 | 04:55 | 13.69 |
| 26 | 340 | 04:55 | 3.40 |
| 27 | 313 | 04:55 | 8.06 |
| 28 | 365 | 05:50 | 2.70 |
| 29 | 392 | 05:30 | 14.40 |
| 30 | 319 | 06:10 | 11.18 |
| 31 | 344 | 06:10 | 8.31 |
| 32 | 309 | 06:20 | 10.12 |
|  |  | Average | 20.35 |

Example 3

Comparison

| Sample no. | Animal no. | Morning milking time | Melatonin in pg/ml |
|---|---|---|---|
| 1 | 386 | 3.10-4.10 | 8.06 |
| 2 | 375 | 3.10-4.10 | 5.63 |

-continued

| Sample no. | Animal no. | Morning milking time | Melatonin in pg/ml |
|---|---|---|---|
| 3 | 363 | 3.10-4.10 | 5.06 |
| 4 | 370 | 3.10-4.10 | 7.18 |
| 5 | 265 | 3.10-4.10 | 3.58 |
| 6 | 34 | 3.10-4.10 | 3.51 |
| 7 | 301 | 3.10-4.10 | 4.35 |
| 8 | 383 | 3.10-4.10 | 3.90 |
| 9 | 314 | 3.10-4.10 | 3.60 |
| 10 | 17 | 3.10-4.10 | 1.91 |
| 11 | 250 | 3.10-4.10 | 9.47 |
| 12 | 247 | 3.10-4.10 | 5.72 |
| 13 | 305 | 3.10-4.10 | 5.88 |
| 14 | 286 | 3.10-4.10 | 4.40 |
| 15 | 205 | 3.10-4.10 | 6.41 |
| 16 | 382 | 3.10-4.10 | 8.24 |
| 17 | 322 | 3.10-4.10 | 3.98 |
| 18 | 392 | 3.10-4.10 | 5.24 |
| 19 | 330 | 3.10-4.10 | 6.60 |
| 20 | 142 | 3.10-4.10 | 1.47 |
| 21 | 303 | 3.10-4.10 | 2.40 |
| 22 | 241 | 3.10-4.10 | 1.52 |
| 23 | 296 | 3.10-4.10 | 4.99 |
| 24 | 340 | 3.10-4.10 | 3.50 |
| 25 | 405 | 3.10-4.10 | 7.10 |
| 26 | 316 | 3.10-4.10 | 0.36 |
| 27 | 345 | 3.10-4.10 | 4.65 |
| 28 | 411 | 3.10-4.10 | 4.94 |
| 29 | 344 | 3.10-4.10 | 3.74 |
| 30 | 365 | 3.10-4.10 | 3.21 |
| 31 | 309 | 3.10-4.10 | 3.48 |
| 32 | 319 | 3.10-4.10 | 2.31 |
| | | Average | 4.57 |

What is claimed is:

1. A method for the production of milk with increased melatonin content relative to a time before the method is performed, or a milk product made therefrom, wherein the method comprises
   (a) dividing a daily cycle of at least one lactating female mammal into a daytime phase under a first light regime, a portion of light of the daytime phase being blue light, and a night-time phase under a second light regime;
   (b) exposing the mammal to the first light regime during the daytime phase;
   (c) exposing the mammal to the second light regime during the night-time phase; and
   (d) milking the mammal at least once during the night-time phase to obtain the milk with increased melatonin content;
   and wherein at least one light source which emits light in a wavelength range of 500 nm or above and substantially no light in a wavelength range below 500 nm is used for the second light regime.

2. The method of claim 1, wherein the at least one light source exhibits at least one maximum relative intensity above 550 nm in a wavelength range of visible light.

3. The method according of claim 1, wherein the at least one light source comprises a luminescent radiator.

4. The method of claim 3, wherein the at least one light source comprises at least one of an LED lamp and a sodium vapor lamp.

5. The method of claim 4, wherein the LED lamp emits red, yellow, orange or amber-coloured light or a mixed color thereof.

6. The method of claim 5, wherein the LED lamp emits red light.

7. The method of claim 1, wherein the at least one female mammal comprises at least one of a sheep, a goat and a cow.

8. The method of claim 1, wherein the at least one female mammal is milked at least twice during a 24-hour period and wherein milk obtained during the daytime phase is not used for providing the milk with increased melatonin content.

9. The method of claim 1, wherein the at least one light source is used in the night-time phase at least during a milking process.

10. The method of claim 1, wherein the at least one light source is used for at least two hours during the night-time phase.

11. The method of claim 1, wherein the at least one light source is used for at least six hours during the night-time phase.

12. The method of claim 1, wherein for the first light regime in the daytime phase sunlight or one or more full-spectrum lamps are used.

13. The method of claim 1, wherein the daytime phase lasts longer than 14 hours.

14. The method of claim 1, wherein the method further comprises extracting lactose from the milk and/or carrying out a fat reduction of the milk.

15. The method of claim 1, wherein the at least one light source produces a luminous intensity of more than 50 lux.

16. The method of claim 15, wherein the at least one light source produces a luminous intensity of more than 100 lux.

17. The method of claim 1, wherein the milk obtained according to (d) has a melatonin content of more than 10 pg/ml.

18. The method of claim 17, wherein the milk obtained according to (d) has a melatonin content of from 15 to 50 pg/ml.

19. The method of claim 1, wherein the method further comprises converting the milk enriched with melatonin to milk powder.

20. The method of claim 19, wherein the milk powder has a melatonin concentration of more than 150 pg/g.

21. The method of claim 19, wherein the milk powder has a melatonin concentration of more than 200 pg/g.

22. A method for the production of milk with increased melatonin content relative to a time before the method is performed, or a milk product made therefrom, wherein the method comprises
   (a) dividing a daily cycle of at least one lactating female mammal into a more than 14 hour long daytime phase under a first light regime, a portion of light of the daytime phase being blue light, and a night-time phase under a second light regime;
   (b) exposing the mammal to the first light regime during the daytime phase;
   (c) exposing the mammal to the second light regime during the nighttime phase; and
   (d) milking the mammal at least once during the night-time phase to obtain the milk with increased melatonin content;
   and wherein at least one light source which produces a luminous intensity of more than 100 lux and emits light in a wavelength range of 500 nm or above and substantially no light in a wavelength range below 500 nm and exhibits at least one maximum relative intensity above 550 nm in a wavelength range of visible light is used for the second light regime for at least two hours.

23. The method of claim 22, wherein the at least one female mammal is milked at least twice during a 24-hour period and wherein milk obtained during the daytime phase is not used for providing the milk with increased melatonin content.

24. The method of claim 22, wherein the milk obtained according to (d) has a melatonin content of more than 10 pg/ml.

25. The method of claim 22 wherein the daytime phase lasts about 16 to 18 hours.

* * * * *